(12) United States Patent
Jayaraman

(10) Patent No.: US 7,081,346 B2
(45) Date of Patent: Jul. 25, 2006

(54) METHOD OF SCREENING BINDING OF A COMPOUND TO A RECEPTOR

(75) Inventor: Vasanthi Jayaraman, Milwaukee, WI (US)

(73) Assignee: Marquette University, Milwaukee, WI (US)

( * ) Notice: Subject to any disclaimer, the term of this patent is extended or adjusted under 35 U.S.C. 154(b) by 710 days.

(21) Appl. No.: 10/145,002

(22) Filed: May 14, 2002

(65) Prior Publication Data

US 2003/0215959 A1 Nov. 20, 2003

(51) Int. Cl.
*G01N 33/53* (2006.01)
*C07K 14/00* (2006.01)

(52) U.S. Cl. .................. 435/7.1; 435/7.93; 530/350
(58) Field of Classification Search ............... 435/7.1, 435/7.93
See application file for complete search history.

(56) References Cited

U.S. PATENT DOCUMENTS

| 3,992,378 A | 11/1976 | St. Clair et al. |
| 4,812,458 A | 3/1989 | Honore et al. |
| 5,208,145 A | 5/1993 | Rogers |
| 2002/0006925 A1 | 1/2002 | Pei et al. |

FOREIGN PATENT DOCUMENTS

| GE | 2451049 | 4/1976 |
| GE | 2847285 | 5/1980 |
| JP | 45/25387 | 8/1970 |
| PL | 91909 | 2/1975 |
| WO | WO 01/79181 A2 | 4/2001 |

OTHER PUBLICATIONS

Madden et al., J. Biol. Chem. 276: 37821-37826, 2001.*
Long et al., (1990) Effect of 6-cyano-2,3-dihydroxy-7-nitro-quinoxaline (CNQX) on dorsal root-, NMDA, kainate- and quisqualate-mediated depolarization of rat motoneurons in vitro, *Br. J. Pharmacol.*, 100:850.
Nakanishi, (1992) Molecular diversity of glutamate receptors and implications for brain functions, *Science*, 258:597.
Armstrong, N. & Gouaux, E. (2000) Mechanisms for activation and antagonism of an AMPA-sensitive glutamate receptor: crystal structures of the FluR2 ligand binding core, *Neuron*, 28:165-181.
Boulter, J. et al., (1990) Molecular cloning and functional expression of glutamate receptor subunit genes, *Science*, 249:1033-1037.
Chen, G.Q. & Gouaux, E. (1997) Overexpression of a glutamate receptor (GluR2) ligand binding domain in *Escherichia coli*: application of a novel protein folding screen, *Proc. Natl. Acad. Sci. USA*, 94:13431-13436.
Gill et al., (1992) The neuroprotective actions of 2,3-dihydroxy-6-nitro-7 sulfamoylbenzo-(f)-quinoxaline (NBQX) in a rat focal ischaemia model, *Brain Res.*, 580:35.

Hollman, M., O'Shea-Greenfield, A., Rodgers, S.W. & Heinemann, S. (1989) Cloning by functional expression of a member of the glutamate receptor family, *Nature*, 342:643-648.
Hollman, M. & Heinemann, S. (1994) Cloned Glutamate receptors, *Annu, Rev. Neurosci.*, 17:31-108.
Honoré et al., (1988) Quinoxalinediones: potent competitive non-NMDA glutamate receptor antagonists, *Science*, 241:701.
Ichord, R.N., Johnston, M.V. & Traystman, R.J. (2001) MK801 decreases glutamate release and oxidative metabolism during hypoglycemic coma in piglets, *Brain Res. Dec. Brain Res.*, 128:139-148.
Keinänen, K. et al., (1990) A family of AMPA-selective glutamate receptors, *Science* 249:556-560.
King et al., (1992) Antagonism of synaptic potentials in ventral horn neurons by 6-cyano-7nitroquinoxaline-2,3-dione: a study in the rat spinal cord in vitro, *Br. J. Pharmacol.*, 107:375.
Knöpfel et al., (1995) Metabrotropic glutamate receptors: novel targets for drug development, *J. Med. Chem.*, 38:1417.
Namba et al, (1994) Antiepileptogenic and anticonvulsant effects of NBQX, a selective AMPA receptor antagonist, in the rat kindling model of epilepsy, *Brain Res.*, 638:36.
Pin and Duvoisin, (1995) The metabotropic glutamate receptors: structure and functions, *Neuropharmacology*, 34:1.
Pringle, A.K., Self, J. & Iannotti, F. (2000) Reducing conditions produce a loss of neuroprotective efficacy of competitive but not non-competitive antagonists in a model of NMDA-mediated excitotoxicity in organotypic hippocampal slice cultures, *Acta. Neurchir. Suppl.*, 76:79-80.
Rao, V.L., Fogan, A., Todd, K.G., Bowen, K.K. & Dempsey, R.J. (2001) Neuroprotection by memantine, a non-competitive NMDA receptor antagonist after traumatic brain injury in rats, *Brain Res.*, 911:96-100.
Saito et. al., (1967) Chemical Studies on Riboflavin and Related Compounds. I. Oxidation of Quinoxaline-2,3-diols as a Possible Model for the Biological Decomposition of Riboflavin, *Biochemistry*, 6(11):3602-3608.

(Continued)

Primary Examiner—Eileen O'Hara
Assistant Examiner—Gyan Chandra
(74) *Attorney, Agent, or Firm*—Joseph T. Leone, Esq.; DeWitt Ross & Stevens S.C.

(57) ABSTRACT

Disclosed is a method of measuring affinity of a test compound for a receptor protein. The method includes the steps of providing a receptor-ligand complex comprising a receptor and a quinoxaline derivative ligand bound thereto; then contacting the receptor-ligand complex with a test compound, thereby yielding a receptor-test compound complex and an amount of free quinoxaline derivative; and then measuring the amount of the free quinoxaline derivative generated as a result of the previous step. In this fashion, the affinity of the test compound for the receptor can be determined.

7 Claims, 2 Drawing Sheets

OTHER PUBLICATIONS

Sheardown et al., (1993) The pharmacology of AMPA receptors and their antagonists, *Stroke 24, Suppl. I*, 146.

Uchida, K. et al., (2001) Dizocilpine but not ketamine reduces the volume of ischaemic damage after acute subdural haemotama in the rat, *Eur. J. Anaesthesiol.*, 18:295-302.

Watkins et al., (1990) Structure-activity relationships in the development of excitatory amino acid receptor agonists and competitive antagonists, *TiPS*, 11:25.

Wisden, W. & Seeburg, P.H., (1993) Mammalian ionotropic glutamate receptors, *Curr. Opin. Neurobio.* 3:291-298.

Yoneda, Y. et al., (2001) Synthesis of diaminobutane derivatives as potent CA(2+)- permeable AMPA receptor antagonists, *Bioorg. Med. Chem. Lett.*, 11:2663-2666.

Zeman and Lodge, (1992) Pharmacological characterization of non-NMDA glutamate subtypes of glutamate receptors in the neonatal rat hemisected spinal cord in vitro, *Br. J. Pharmacol.*, 106:367.

* cited by examiner

US 7,081,346 B2

METHOD OF SCREENING BINDING OF A COMPOUND TO A RECEPTOR

FIELD OF THE INVENTION

The invention is detecting whether a chosen compound binds to a chosen neurotransmitter receptor.

BACKGROUND

Ionotropic glutamate receptors are the predominant mediators of excitatory synaptic signals in the mammalian central nervous system. Glutamate binding triggers the formation of transmembrane ion channels in the receptor protein, permitting cations to flow down the resultant electrochemical gradients and across the postsynaptic membrane, thus depolarizing it, and thereby stimulating the receiving cell. In addition to synaptic transmission, the glutamate receptors play an important role in the regulation of synaptic strength and in diverse neuropathologies, including epilepsy and stroke (reviewed in 1). According to agonist affinity profiles, these receptors can be subdivided into three subfamilies: α-amino-5-methyl-3-hydroxy-4-isoxazole propionate (AMPA) receptors, N-methyl-D-aspartate (NMDA) receptors, and kainate receptors (1, 2). Because there is significant cross-reactivity between the ligands that activate the AMPA and kainate receptors, these two receptor types are grouped together under the term "non-NMDA glutamate" receptors (3–5).

Antagonists of all the three subtypes of the ionotropic glutamate receptor have been found to have protective effects against both chronic and acute neurodegenerative processes in animal models (6–11). Most of the current research has been focused on the NMDA antagonists. Antagonists of non-NMDA glutamate receptors have not been explored to the same extent.

At present, two methods are conventionally used for screening for compounds that bind to receptor proteins such as glutamate receptors, namely radioactive ligand binding (12) and electrophysiological current recording measurements (13). In the radioactive ligand binding method, competitive displacement of a radioactive ligand (such as $^3$H-AMPA) by the test compound is used as the basis for determining the affinity of the test compound to the receptor. In the electrophysiological method, the function of the compound in activating or deactivating the receptor (as measured by the ionic currents mediated by the receptor) is used as the basis for determining the affinity of the test compound to the receptor. As a general proposition, radioactive ligand binding is the more commonly used method because it is less time consuming relative to electrophysiological approach. There remains, however, a long-felt and unmet need for a ligand-binding assay that is as fast or faster than the radioactive ligand binding method (while maintaining comparable accuracy and precision), but that does not require the use of radioactive reagents. Such an alternative is the subject of the present invention.

SUMMARY OF THE INVENTION

The present invention is a method of screening compounds for their ability to bind to non-NMDA glutamate receptors. The method is fast, accurate, precise, and does not require radioactive reagents. The method can be implemented in a combinatorial fashion and automated for high-throughput screening. The method is useful for screening drug candidates for their ability to bind to non-NMDA glutamate receptors, and thus finds use in the screening of neuroprotective drugs and drug candidates.

Compounds that bind competitively to the agonist binding site of non-NMDA glutamate receptors can be screened by competition experiments with quinoxaline derivatives that are bound either to the soluble ligand binding domain of the non-NMDA glutamate receptor protein or to mouse cortical neurons that inherently have a high concentration of non-NMDA glutamate receptors. The assay is based on the fact that quinoxaline derivatives exhibit different absorption spectral features in the visible region (310 nm to 450 nm) in the bound and free forms. Hence, a test compound that displaces the bound quinoxaline from the receptor will display a pronounced effect in spectra of the receptor-quinoxaline complex taken in the absence of the test compound versus in the presence of the test compound.

The invention described and claimed herein thus is a safer, cheaper, and equally precise and accurate alternative method for assay ligand binding to non-NMDA glutamate receptors as compared to assay methods that require the use of radioactive reagents.

In the preferred embodiment, the invention is a method of measuring affinity of a test compound for a receptor protein. The method comprises first providing a receptor-ligand complex comprising a receptor and a quinoxaline derivative ligand bound thereto. The receptor-ligand complex is then contacted with a test compound under conditions and for a time sufficient to allow the test compound to bind to the receptor, thereby yielding a receptor-test compound complex and an amount of free quinoxaline derivative. The amount of the free quinoxaline derivative generated as a result of the previous step is then measured, whereby the affinity of the test compound for the receptor is determined.

Alternatively, the inventive method can be implemented by first providing a receptor-test compound complex comprising a non-NMDA glutamate receptor and a test compound bound thereto. The receptor-test compound complex is then contacted with a known concentration of a quinoxaline derivative under conditions and for a time sufficient to allow the quinoxaline derivative to bind to the receptor, thereby yielding a receptor-quinoxaline complex and an amount of free quinoxaline derivative. The amount of the free quinoxaline derivative generated as a result of the previous step is measured and the amount of the free quinoxline is compared to the known concentration of quinoxaline originally added to the reaction, whereby the affinity of the test compound for the receptor is determined.

In both approaches, it is preferred that the receptor comprises a non-NMDA glutamate receptor.

It is also preferred that the quinoxaline derivative be selected from the group consisting of a compound of Formula I:

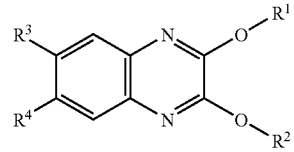

Formula I wherein $R^1$ and $R^2$ are independently selected from the group consisting of hydrogen; halo, substituted or unsubstituted alkyl, alkenyl, alkynyl; substituted or unsubstituted heteroalkyl; acyl; and substituted or unsubstituted aryl; and $R^3$ and $R^4$ are independently selected from the group consisting of hydrogen, hydroxy, halo; substituted or unsubstituted alkyl, alkenyl, alkynyl; substituted or unsubstituted heteroalkyl; acyl, carboxy, cyano, cyanoalkyl, nitro, amino, sulfonyl, alkylsulfonyl, amido, and sulfonamido. The most preferred quinoxalines are those wherein $R^1$ and $R^2$ are hydrogen.

Another embodiment of the invention is a method of measuring affinity of a test compound for a non-NMDA glutamate receptor protein. Here, the method comprises first contacting a non-NMDA glutamate receptor with a known amount of a quinoxaline derivative under conditions and for a time sufficient to allow at least a portion of the quinoxaline derivative to bind to the receptor, thereby yielding a receptor-quinoxaline complex and a first amount of free quinoxline derivative. A visible spectrum of the free quinoxline from the previous step is then recorded. The complex is then contacted with a test compound under conditions and for a time sufficient to allow the test compound to bind to the receptor, thereby displacing at least a portion of the quinoxaline derivative from the complex and yielding a receptor-test compound complex and a second amount of free quinoxaline derivative. A visible spectrum of the second amount of free quinoxline derivative is then taken. The two recorded spectra are then compared, whereby the affinity of the test compound for the receptor is determined.

DETAILED DESCRIPTION OF THE INVENTION

Figure 1:
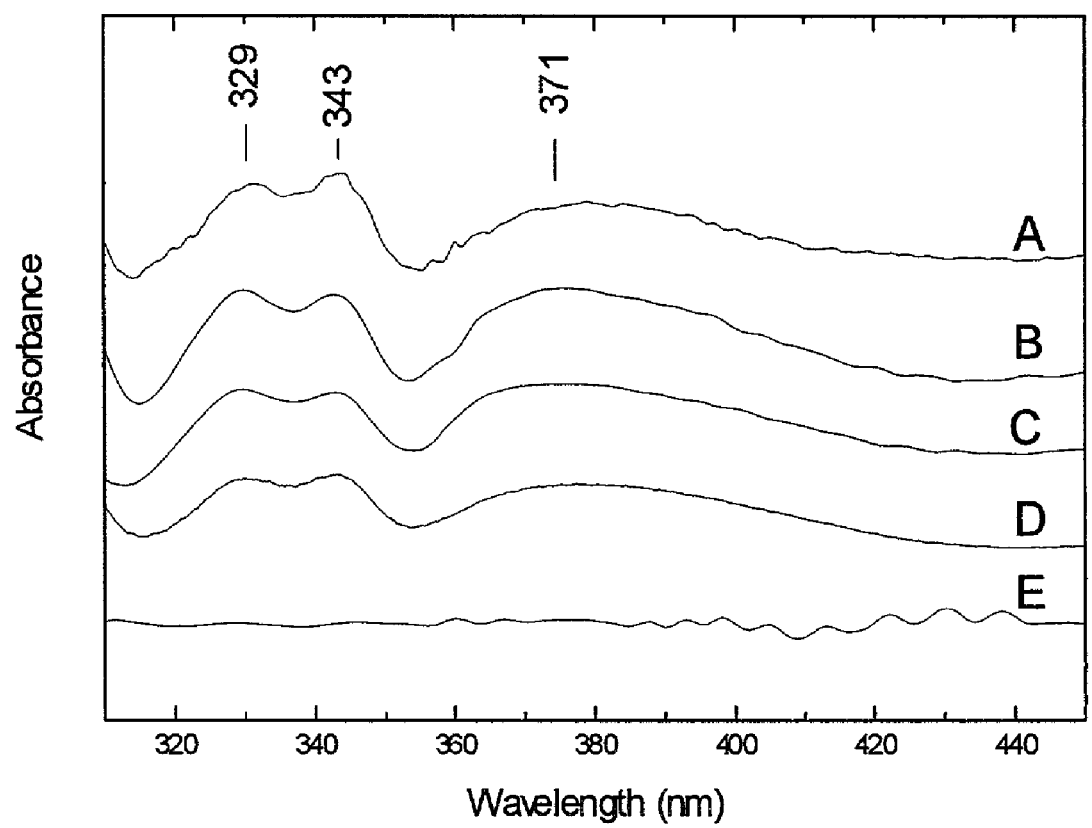
FIG. 1: (A) Difference spectrum between the free CNQX in buffer and CNQX bound to GluR2-S1S2 (B) Difference spectrum between the GluR2-S1S2 protein in complex with 25 µM CNQX in the presence of α-amino-3-hydroxy-5-methylisoxazole-4-propionic acid (AMPA) and absence of AMPA. (C) Difference spectrum between the GluR2-S1S2 protein in complex with 25 µM CNQX in the presence of glutamate and absence of glutamate. (D) Difference spectrum between the GluR2-S1S2 protein in complex with 25 µM CNQX in the presence of kainate and absence of kainate. (E) Difference spectrum between the GluR2-S1S2 protein in complex with 25 µM CNQX in the presence of γ-amino butyric acid and absence of γ-amino butyric acid.

Quinoxaline derivatives are a class of competitive antagonists of the non-NMDA glutamate receptors. Quinoxaline-based compounds compete for the same binding site on the protein as the agonists glutamate, AMPA and kainate. The present invention is based on the newly discovered fact that these quinoxaline derivatives, such as 6-cyano-7-nitro-2,3-dihydroxyquinoxaline (CNQX) and the others described herein, have a different and distinct absorption spectrum in free solution versus the spectrum of the same quinoxaline derivative when bound to the receptor protein. Therefore, when a compound to be tested binds to the same receptor site as the quinoxaline derivative, the test compound displaces the bound quinoxaline derivative into the solution. In other words, the test compound raises the concentration of the free quinoxaline derivative in solution. This increase is easily detected via corresponding changes in the absorption spectrum.

Quinoxaline and Quinoxaline Derivatives:

The present invention relies upon the ability of quinoxaline and quinoxaline derivatives to bind to receptor proteins in general and non-NMDA glutamate receptor proteins in particular. As used herein, the term "quinoxaline derivative" explicitly encompasses any and all compounds (substituted or unsubstituted) having a quinoxaline core and which are capable of binding to non-NMDA glutamate receptor proteins. Thus, the term "quinoxaline derivative" as used herein encompasses quinoxaline itself and any and all substituted quinoxaline derivatives, analogs, isomers, enantiomers, diastereomers, etc., of any and all stereochemical conformations (including racemic mixtures, isolated enantiomers or diastereomers, or enantiomerically-enriched mixtures of the compounds).

Quinoxaline (systematic name 1,4-benzodiazine) has the following structure and positional numbering scheme:

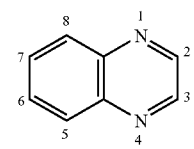

Quinoxaline (also known as 1,4-benzodiazine)

Quinoxaline itself is an article of commerce and can be purchased from numerous national and international suppliers, including Sigma-Aldrich Chemicals (St. Louis, Mo.) and Tocris-Cookson Inc. (Ellisville, Mo. and Bristol, England).

The preferred quinoxaline derivatives for use in the present invention are those of Formula I:

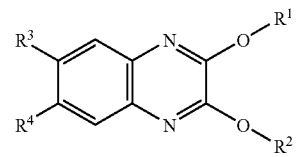

Formula I wherein $R^1$ and $R^2$ are independently selected from the group consisting of hydrogen; halo, substituted or unsubstituted alkyl, alkenyl, alkynyl; substituted or unsubstituted heteroalkyl; acyl; and substituted or unsubstituted aryl; and $R^3$ and $R^4$ are independently selected from the group consisting of hydrogen, hydroxy, halo; substituted or unsubstituted alkyl, alkenyl, alkynyl; substituted or unsubstituted heteroalkyl; acyl, carboxy, cyano, cyanoalkyl, nitro, amino, sulfonyl, alkylsulfonyl, amido, and sulfonamido.

Where $R^1$ and $R^2$ are both hydroxy, the corresponding dione compounds are also included within the scope of "quinoxaline derivatives." In other words, where the quinoxaline core is 2,3-dihydroxy substituted, these compounds readily shift between a "diol" form and a "dione" form:

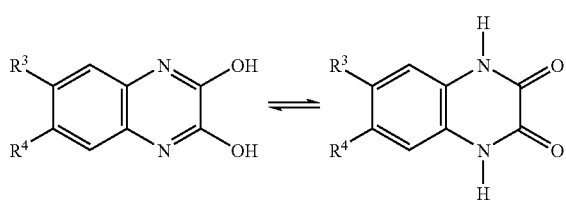

For purposes of the invention disclosed herein, these two forms of the quinoxaline derivative are synonymous and are explicitly included within the scope of the term "quinoxaline derivative."

As used in this application, the designations for groups $R^1$ through $R^4$ are to be given the following definitions: The term "alkyl," by itself or as part of another substituent, means, unless otherwise stated, a fully saturated, straight, branched chain, or cyclic hydrocarbon radical, or combination thereof, and can include di- and multi-valent radicals, having the number of carbon atoms designated (e.g., $C_1$–$C_{10}$ means from one to ten carbon atoms, inclusive). Examples of alkyl groups include, without limitation, methyl, ethyl, n-propyl, isopropyl, n-butyl, t-butyl, isobutyl, sec-butyl, cyclohexyl, (cyclohexyl)ethyl, cyclopropylmethyl, and homologs, and isomers thereof, for example, n-pentyl, n-hexyl, n-heptyl, n-octyl, and the like. The term "alkyl," unless otherwise noted, also includes those derivatives of alkyl defined in more detail below as "heteroalkyl" and "cycloalkyl."

The term "alkenyl" means an alkyl group as defined above containing one or more double bonds. Examples of alkenyl groups include vinyl, 2-propenyl, crotyl, 2-isopentenyl, 2-(butadienyl), 2,4-pentadienyl, 3-(1,4-pentadienyl), etc., and higher homologs and isomers.

The term "alkynyl" means an alkyl or alkenyl group as defined above containing one or more triple bonds. Examples of alkynyl groups include ethynyl, 1- and 3-propynyl, 3-butynyl, and the like, including higher homologs and isomers.

Typically, alkyl, alkenyl, and alkynyl, groups will have from 1 to 24 carbon atoms. Those groups having 10 or fewer carbon atoms are preferred in the present invention. The term "lower" when applied to any of these groups, as in "lower alkyl" or "lower alkylene," designates a group having 10 or fewer carbon atoms.

"Substituted" refers to a chemical group as described herein that further includes one or more substituents, such as lower alkyl, aryl, acyl, halogen (e.g., alkylhalo such as $CF_3$), hydroxy, amino, alkoxy, alkylamino, acylamino, sulfonamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl, alkenyl, or alkynyl moieties. Additionally, these groups may be pendent from, or integral to, the carbon chain itself.

The term "heteroalkyl," by itself or in combination with another term, means, unless otherwise stated, a stable, saturated or unsaturated, straight, branched chain, or cyclic hydrocarbon radical, or combinations thereof, consisting of the stated number of carbon atoms and from one to three heteroatoms selected from the group consisting of O, N, Si, and S, and wherein the nitrogen and sulfur atoms may optionally be oxidized and the nitrogen heteroatom(s) may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as in —$CH_2$—NH—O—$CH_3$ and —$CH_2$—O—Si($CH_2$)$_3$. Explicitly included within the term "heteroalkyl" are those radicals that could also be described "heterocycloalkyl" (i.e., containing a cyclic group). The term "heteroalkyl" also explicitly includes unsaturated groups (i.e., heteroalkenyls and heteroalkynyls).

The term "aryl" is used herein to refer to an aromatic substituent, which may be a single aromatic ring or multiple aromatic rings which are fused together, linked covalently, or linked to a common group such as a diazo, methylene or ethylene moiety. The common linking group may also be a carbonyl as in benzophenone. The aromatic ring(s) may include, for example phenyl, naphthyl, biphenyl, diphenylmethyl and benzophenone, among others. The term "aryl" encompasses "arylalkyl" and "substituted aryl." For phenyl groups, the aryl ring may be mono-, di-, tri-, tetra-, or penta-substituted. Larger rings may be unsubstituted or bear one or more substituents.

"Substituted aryl" refers to aryl as just described including one or more functional groups such as lower alkyl, acyl, halogen, alkylhalo (e.g., $CF_3$), hydroxy, amino, alkoxy, alkylamino, acylamino, acyloxy, phenoxy, mercapto, and both saturated and unsaturated cyclic hydrocarbons which are fused to the aromatic ring(s), linked covalently or linked to a common group such as a diazo, methylene, or ethylene moiety. The linking group may also be a carbonyl such as in cyclohexyl phenyl ketone. The term "substituted aryl" encompasses "substituted arylalkyl."

The term "acyl" is used to describe an aldehyde or ketone substituent, —C(O)R, where R is hydrogen or a substituted or unsubstituted alkyl, alkenyl, alkynyl, or aryl as defined herein. The term "carboxy" refers to an ester linkage or group or a carboxylic acid, i.e., —C(O)O—, —C(O)—OR, R—C(O)O— or —C(O)—OH.

The term "halogen" or "halo" is used herein to refer to fluorine, bromine, chlorine and iodine atoms.

The term "hydroxy" refers to the group —OH. "Nitro" refers to the group —$NO_2$.

The term "amino" is used to designate —NRR', wherein R and R' are the same or different and are independently H, alkyl, alkenyl, alkynyl, aryl or substituted analogs thereof "Amino" encompasses "alkylamino," denoting secondary and tertiary amines. "Acylamino" or "amido" designates the group RC(O)NR'. "Sulfonamido" designated the group —$SO_2$NRR'.

The most preferred quinoxaline derivatives for use in the present invention are those having a 2,3-dihydroxy-6,7-substituted pattern, wherein the moieties at the 6 and 7 positions can be selected from a wide variety of groups. Preferred from among these 2,3-dihydroxy quinoxline derivatives are the compounds designated CNQX, DNQX, and NBQX. The structures of these three compounds, as well as their systematic names, are as follows:

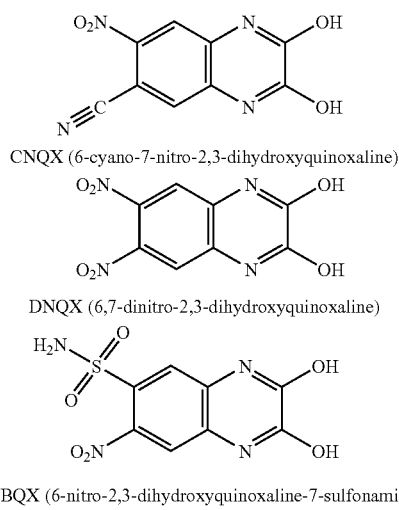

CNQX (6-cyano-7-nitro-2,3-dihydroxyquinoxaline)

DNQX (6,7-dinitro-2,3-dihydroxyquinoxaline)

NBQX (6-nitro-2,3-dihydroxyquinoxaline-7-sulfonamide)

Explicitly included within the above definitions of CNQX, DNQX, and NBQX (as well as all other 2,3-dihydroxy substituted quinoxaline derivitaves described herein) are the corresponding 2,3-dione quinoxaline derivatives (i.e., 2,3-quinoxalones).

CNQX, DNQX, and NBQX are all available commercially from such sources as Sigma-Aldrich Chemical and Tocris-Cookson Inc. For papers describing the synthesis and properties of CNQX, see references 17–20. For papers describing the synthesis and properties of DNQX, see references 21–24. For papers describing the synthesis and properties of NBQX, see references 25–28. See also U.S. Pat. No. 4,812,458.

Sigma-Aldrich and Tocris-Cookson also commercially supply a broad range of the above-noted quinoxaline derivatives including 2-quinoxalinecarboxylic acid, 2-quinoxalinecarbonyl chloride, 2-hydroxyquinoxaline (i.e., 2-quinoxalinol), 2,3-dihydroxyquinoxaline, and 6,7-dichloro-2,3-dihydroxyquinoxaline.

A number of quinoxaline derivatives that can be used in the present invention are also described in the patent literature. Specifically, U.S. Pat. No. 3,992,378 describes 6,7-dimethyl-2,3-dihydroxyquinoxaline and several mono- and 5,7-disubstituted 2,3-dihydroxyquinoxaline compounds. 6-Chloro-7-carboxy-2,3-dihydroxyquinoxaline is described as having activity against peptic ulcers in South African Patent No. 67/7613. 6-Methyl-7-carboxy-2,3-dihydroxyquinoxaline is described in *Biochemistry*, 6(11), 3602–8 (1967). 6-Methyl-7-methoxy-2,3-dihydroxyquinoxaline is described in Japanese Patent No. 45/25387. 6-Amino-7-nitro-2,3-dihydroxyquinoxaline is described in German Patent No. 2,451,049. 6-Nitro-7-methoxy-2,3-dihydroxyquinoxaline is described in Polish Patent No. 91909. 6-Amino-7-methoxy-2,3-dihydroxyquinoxaline and 6-amino-7-methyl-2,3-dihydroxyquinoxaline are described in Polish Patent No. 93835. 6-Amino-7-carbomethoxy-2,3-dihydroxyquinoxaline is described in German Patent No. 3106111 as having various industrial and research uses. 6-Amino-7-chloro-2,3-dihydroxy quinoxaline is disclosed in German Patent No. 2,847,285 as an intermediate in the preparation of azo dyes.

A general syntheses of various quinoxaline derivatives proceed as follows:

In a first synthetic approach, a compound of Formula II:

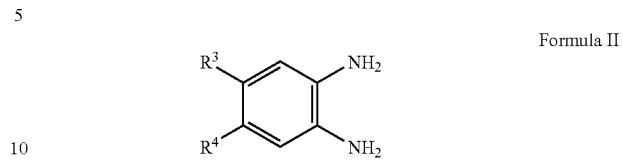

Formula II (where $R^3$ and $R^4$ are as defined above) is reacted with oxalate or a reactive oxalate derivative to form a quinoxline derivative of Formula I.

A second synthetic approach comprises nitrating a compound of Formula III:

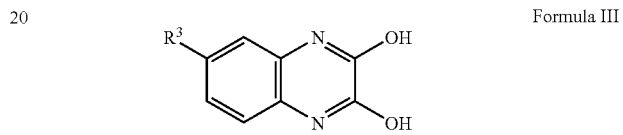

Formula III where $R^3$ is as defined above, thereby to yield a quinoxaline derivative of Formula I wherein $R^4$ is nitro.

In a third synthetic approach, a compound of Formula IV:

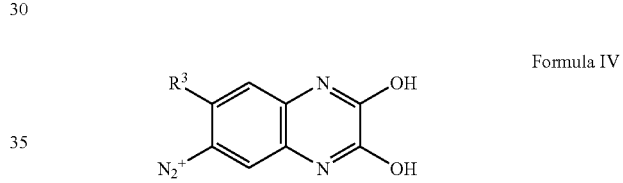

Formula IV where $R^3$ is as defined above, is reacted with potassium tetracyanonickelate to form a quinoxline derivative of Formula I wherein $R^4$ is cyano.

A fourth synthetic approach is to react a compound of Formula V:

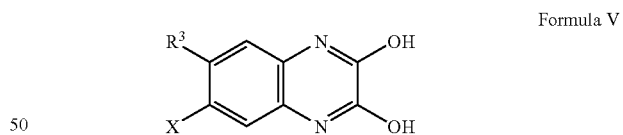

Formula V wherein $R^3$ is halogen, CN, $CF_3$, $N_3$, $SO_2$, $C_1$–$C_3$-alkyl, or $NO_2$, and wherein X is halogen, with trialkylsilylacetylene, and hydrolyzing the intermediate compound, thereby yielding a quinoxaline derivative of Formula I.

A fifth synthetic approach is to reduce a compound of Formula VI:

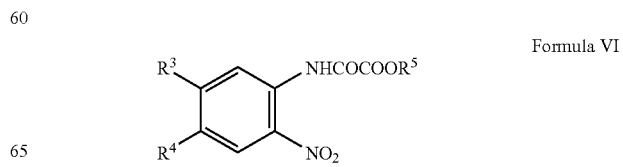

Formula VI where $R^3$ and $R^4$ are as defined above, and wherein $R^5$ is alkyl, to form a compound of Formula I.

Examples of the how the above-described synthetic approaches can be used to make quinoxline derivatives for use in the present inveniton are as follows:

6-Bromo-2,3-dihydroxy-7-nitroquinoxaline: To a solution of 0.5 g (2.1 mmol) of 6-bromo-2,3-dihydroxyquinoxaline in 5 ml of concentrated sulfuric acid at 0° C. is added 210 mg (2.1 mmol) $KNO_3$. The solution is stirred at 0° C. for 30 min. and at 24° C. for 3 h. The reaction mixture is poured into ice-water, giving 5 g precipitate. The crude product is dissolved in 30 ml of hot 2N NaOH. 4N HCl is added, adjusting the pH to 2, thereby yielding 6-bromo-2,3-dihydroxy-7-nitroquinoxaline. NMR: two singlets (7.3 and 7.7 ppm downfield from TMS).

6-Cyano-2,3-dihydroxy-7-nitroquinoxaline: 1 g of 6-Cyano-2,3-dihydroxy-quinoxaline is added gradually to 10 ml of ice-cold fuming nitric acid. The mixture is stirred at 25° C. for 1 h. The reaction mixture is poured into ice-water giving 1 g of a crude product. Recrystallization (dimethylformamide-water) gives 0.9 g (75%) of 6-cyano-2,3-dihydroxy-7-nitroquinoxaline. IR: peak at 2240 $cm^{-1}$; NMR: two singlets (7.7 and 8.2 ppm downfield from TMS).

6-Azido-2,3-dihydroxyquinoxaline: A solution of 5 g (23.5 mmol) 6-amino-2,3-dihydroxyquinoxaline hydrochloride in 250 ml 0.5 N $H_2SO_4$ is cooled to 0° C. and then a solution of 1.65 g (24 mmol) $NaNO_2$ in 50 ml water is added. After stirring at 0° C. for 15 min., a solution of 1.5 g (24 mmol) $NaN_3$ in 100 ml water is added. Stirring at 0° C. for 45 min. gives a precipitate of 3 g (67%) 6-azido-2,3-dihydroxyquinoxaline. IR: a peak at 2220 $cm^{-1}$.

6-Azido-2,3-dihydroxy-7-nitroquinoxaline: 2 g 6-azido-2,3-dihydroxyquinoxaline is suspended in 100 ml glacial acetic acid. To the suspension is added 16 ml fuming nitric acid at 24° C. The mixture is stirred at 24° C. for 4 h giving a precipitate of 1.9 g (78%) 6-azido-2,3-dihydroxy-7-nitroquinoxaline. IR: a peak at 2120 $cm^{-1}$. NMR: two singlets (7.0 and 7.7 ppm downfield from TMS).

2,3-Dihydroxy-6-nitro-7-trifluoromethylquinoxaline: A solution of 1 g (4.4 mmol) 2,3-dihydroxy-6-trifluoromethylquinoxaline in 10 ml concentrated $H_2SO_4$ is cooled to 0° C. and 438 mg (4.4 mmol) $KNO_3$ is added. The mixture is stirred at 0° C. for 0.5 h and at 24° C. for 3 h. The reaction mixture is poured into ice-water to give 1.02 g crude product. The crude product is dissolved in 2N NaOH. Addition of 4N HCl to pH 5 gives 0.86 g (72%) 2,3-dihydroxy-6-nitro-7-trifluoromethylquinoxaline. NMR: two singlets (7.5 and 7.8 ppm downfield from TMS).

6-Cyano-2,3-dihydroxy-7-trifluoromethylquinoxaline: To a solution of 680 mg (2.5 mmol) 2,3-dihydroxy-6-nitro-7-trifluoromethylquinoxaline in 2 ml concentrated HCl is added (at 24° C.) a solution of 1.89 g (8 mmol) $SnCl_2 \cdot 2H_2O$ in 4 ml concentrated HCl. The mixture is stirred at 70° C. for 1 h. Addition of 10 ml $H_2O$ and 50% aqueous NaOH to pH 1 gives a precipitate (1.5 g) which on TLC ($CHCl_3:CH_3OH$, 4:1) shows only one spot. The crude product is dissolved in 5 ml concentrated HCl. To the solution is added 60 ml $H_2O$, and a solution of 170 mg (2.5 mmol) $NaNO_2$ in 5 ml $H_2O$ is added (at 0° C.). After stirring at 0° C. for 20 min., saturated $NaHCO_3$ is added to pH 7, followed by a solution of 1.2 g. $K_2Ni(CN)_4$ in 30 ml $H_2O$. The mixture is stirred at 24° C. for 3 h. The reaction mixture is evaporated, and the residue is triturated with acetone to give 200 mg of a crystalline product. Column chromatography (eluent: ethyl acetate containing 5% acetic acid) gives 100 mg (16%) 6-cyano-2,3-dihydroxy-7-trifluoromethylquinoxaline. IR: a peak at 2240 $cm^{-1}$. HMR: two singlets (7.5 and 7.6 ppm downfield from TMS).

6-Chloro-7-methylsulfonyl-2,3-dihydroxyquinoxaline: A solution of 8 g methyl-(2-chloro-5-nitro)phenyl-sulfone (Dickey et al., Ind. Eng. Chem. 45, 1730–33(1953)) in 20 ml acetone and 100 ml ethanol is hydrogenated at atmospheric pressure and at 24° C. using a Ra—Ni catalyst (3 g). Evaporation gives a TLC-pure product. A solution of the crude product in 100 ml acetic anhydride is stirred at 100° C. for 15 min. and at 24° C. for 3 h. The mixture is poured into 500 ml water giving 5.5 g N-acetyl-4-chloro-5-methylsulfonylaniline. The crude N-acetyl-4-chloro-5-methylsulfonyl aniline (4.7 g) is added gradually to 35 ml fuming nitric acid at 0° C. After stirring at 24° C. for 45 min., 100 ml of ice water is added, and the mixture is extracted with 3×100 ml ethyl acetate giving 4 g of a mixture of two compounds (TLC). The compounds are separated using column chromatography. Product I: 1.6 g (29%) N-acetyl-2-nitro-4-chloro-5-methylsulfonylaniline; NMR: two singlets (8.2 and 8.8 ppm downfield from TMS). Product II: 2.0 g (36%) N-acetyl-4-chloro-5-methylsulfonyl-6-nitroaniline; NMR: two doublets (7.7 and 8.1 ppm downfield from TMS). J=ca. 9 Hz).

To a mixture of 25 ml 6N HCl and 8 ml ethanol is added 1.6 g N-acetyl-2-nitro-4-chloro-5-methylsulfonylaniline and the solution is refluxed for 2 h. The reaction mixture is cooled to 24° C. and 50% NaOH is added to pH 12 which gives 0.9 g (65%) of the deacetylated compound. A solution of the crude product in a mixture of 10 ml 4N HCl and 500 ml methanol is hydrogenated at atmospheric pressure by using 5% Pt—C (100 mg) as a catalyst. The crude 1,2-diamino compound in a mixture of 20 ml 4N HCl and 1.6 g oxalic acid dehydrate is refluxed for 2.5 h. Cooling to 24° C. gives a precipitate. The crude product is dissolved in 2N NaOH and precipitated with addition of 4N HCl to pH 2–3 to give 0.4 g 6-chloro-7-methylsulfonyl-2,3-dihydroxyquinoxaline.

6-Chloro-2,3-dihydroxy-7-nitroquinoxaline: Finely powdered potassium nitrate (1.01 g, 10 mmol) is added during 5 min. to a stirred solution of 6-chloro-2,3-dihydroxyquinoxaline (1.97 g, 10 mmol) in 50 ml of concentrated sulfuric acid at 0° C. After 1 h, the ice bath was removed and stirring continued for 2.5 h at room temperature. The mixture is poured into 200 ml of ice/water and the precipitate is isolated, washed with water, ethanol, and ether. The product is dissolved in 70 ml of hot 2N sodium hydroxide, filtered while hot, and reprecipitated with concentrated hypochloric acid to give 2.12 g (88%) of pure title compound. $^3$H-NMR (DMSO-$d_6$): δ 7.23 (s, 1H, H-5); δ 7.82 (s, 1H, h-8); δ 12.1 (broad s, 2H, 2NH).

6-Chloro-7-cyano-2,3-dihydroxyquinoxaline: 6-Amino-7-chloro-2,3-dihydroxy-quinoxaline (0.42 g, 2.0 mmol) is added to 20 ml of stirred, hot 1M HCl, and the resulting solution cooled to 0° C. The finely divided hydrochloride is then diazotized at 0–5° C. with sodium nitrite (0.14 g, 2.0 mmol) in 5 ml of water with vigorous stirring for 30 min. A solution of potassium tetracyanonickelate (1.3 g, 5.4 mmol) in 25 ml of saturated aqueous sodium hydrogen carbonate is added to the resulting mixture with stirring at room temperature. After 3 h, the mixture is cooled on ice and filtered. The product is washed with water, boiled in a mixture of 2N sodium hydroxide (25 ml) and ethanol (50 ml), and filtered while hot. The filtrate is cooled and acidified to pH 1 with concentrated HCl. The resulting precipitate is isolated, washed with water and dried to give 40 mg (9%) of the title product. IR (KBr): 2235(CN), 1700 cm$^{-1}$. $^1$H-HMR (DMSO-d$_6$): δ 7.24 (s, 1H, ArH), δ 7.43 (s, 1H, ArH), δ 12.1 (broad s, 2H, 2NH).

2,3-Dihydroxy-6-trimethylsilylethynyl-7-nitroquinoxaline: A mixture of 500 mg (1.9 mmol) 6-bromo-2,3-dihydroxy-7-nitroquinoxaline (supra) in 10 ml dry dimethylformamide and 20 ml dry triethylamine is added to 4 mg palladium(II)acetate, 8 mg triphenylphosphine and 600 μl (4.3 mmol) trimethylsilylacetylene. The mixture is refluxed for 2.5 h under nitrogen. After cooling to room temperature, the reaction mixture is evaporated in vacuo. The residue is stirred with water, filtered and washed with water to give 500 mg of a crude product. The crude product is dissolved in ethyl acetate and purified by column chromatography (silica gel) to give 400 mg (70%) of 2,3-dihydroxy-6-trimethylsilylethynyl-7-nitroquinoxaline. NMR (DMSO-d$_6$): δ 7.8 (1H, s), δ 7.2 (1H, s), δ 0.3 (9H, s).

6-Ethynyl-2,3-dihydroxy-7-nitroquinoxaline: A solution of 300 mg (0.99 mmol) 2,3-dihydroxy-6-trimethylsilylethynyl-7-nitroquinoxaline in 10 ml methanol is added to 200 mg (1.45 mmol) potassium carbonate and then stirred at room temperature for 1 h. The reaction mixture is evaporated in vacuo and 4N hydrochloric acid is added to pH 6. The precipitated product is filtered off and washed with water to give 200 mg (88%) of 6-ethynyl-2,3-dihydroxy-7-nitroquinoxaline. NMR (DMSO-d$_6$): δ 7.7 (1H, s), δ 7.2 (1H, s), δ 4.5 (1H, s).

4-Ethoxyalylaminophthalodiamide: To a solution of 10 g (56.0 mmol) 4-amino-phthalodiamide in 200 dry dimethylformamide is added 8.5 ml (61.2 mmol) dry triethylamine. A solution of 7.0 ml (61.5 mmol) ethoxyalylchloride in 50 ml dry dimethylformamide is added dropwise. Stirring is continued at 25° C. for 1 h. To the reaction mixture is added 600 ml methanol and the solution cooled to 0° C. The preciptate is filtered off and washed with methanol to give 10.6 g (68%) 4-ethoxalylaminophthalodiamide.

4-Ethoxalylaminophthalodinitrile: To a mixture of 10 g (35.8 mmol) 4-ethoxalylaminophthalodiamide in 100 ml dry pyridine is gradually added 5.9 ml (64.9 mmol) phosphorus oxychloride. Stirring is continued at 25° C. for 30 min. The reaction mixture is then poured into an ice-cold mixture of 100 ml concentrated HCl and 200 ml water to give 6.6 g (76%) 4-ethoxalylaminophthalodinitrile as a precipitate.

4-Ethoxalylamino-5-nitrophthalodinitrile: A solution of 5 g (20.6 mmol) 4-ethoxalylaminophthalodinitrile in 75 ml 100% nitric acid is stirring at 25° C. for 48 h. The reaction mixture is then poured into 500 ml of ice water to give a precipitate (4 g). Column chromatography (silica gel, eluents: toluene containing 25% ethyl acetate) gives 2 compounds: 4-ethoxalylamino-3-nitro-phthalodinitrile (1.9 g). NMR (DMSO-d$_6$): δ 8.5 (1H, d, J=8 HZ), δ 8.3 (1H, d, J=8 HZ); and 4-ethoxalylamino-5-nitrophthalodinitrile (1.9 g); NMR (DMSO-d$_6$): δ 9.0 (1H, s), δ 8.7 (1H, s). The last compound is used in the next step.

6,7-Dicyano-2,3-dihydroxyquinoxaline: A solution of 0.5 g (1.7 mmol) 4-ethoxalylamino-5-nitrophthalodinitrile in a mixture of 50 ml ethanol and 20 ml ethyl acetate is hydrogenated at atmospheric pressure using 5% Pd—C (0.5 g) as a catalyst. The reaction mixture is filtered and evaporated in vacuo. The residue is dissolved in ethyl acetate, and the solution is passed through a short column (silica gel) to give the intermediary product 4-amino-5-ethoxalylaminophthalodinitrile. A solution of this compound in 50 ml ethanol is refluxed 3 h to give 0.2 g (53%) 6,7-dicyano-2,3-dihydroxyquinoxaline as crystals. IR (KBr): 2240 cm$^{-1}$ (CN); NMR (DMSO-d$_6$): δ 12.2 (2H, broad m), δ 7.6 (2H, s).

Quinoxaline Displacement Assay:

The present inventive method is quite straightforward and is based upon difference between the visible spectrum of a quinoxaline derivative in solution (i.e, a free quinoxaline) and the visible spectrum of the same quinoxaline derivative when bound to a receptor. In short, quinoxaline derivatives, such 6-cyano-7-nitro-2,3-dihydroxy-quinoxaline (CNQX), have distinct absorption spectrum in free solution versus the spectrum of the same quinoxaline derivative when bound to the receptor protein. Thus, by comparing a "before-and-after" difference spectrum (i.e., a difference spectrum between the quinoxaline/receptor in the absence of a test compound and the quinoxaline/receptor in the presence of a test compound), it can be determined whether the test compound is capable of displacing the quinoxaline derivative from the receptor. If the test compound binds to the same receptor site as the quinoxaline derivative, the test compound will displace the bound quinoxaline derivative into the solution, thereby giving rise to discernible changes in the visible difference spectrum.

In the preferred embodiment, the reaction is detected using visible absorption spectrophotometry. In the most preferred embodiment, the reaction is monitored at wavelengths from about 310 nm to about 450 nm. Visible spectrophotometry is exceedingly well known in the art and will not be described in any detail herein. A myriad of suitable spectrophotometers are made by numerous commercial suppliers, such as the Agilent-brand and Shimadzu-brand spectrometers mentioned in the Examples section.

To begin, a baseline or control spectrum of the free quinoxaline derivative in buffer solution is generated. A second spectrum is then taken of the quinoxaline admixed with the receptor under investigation. A difference spectrum is then generated between the first spectrum (free quinoxaline) and second spectrum (protein-bound quinoxaline). The characteristic features of this difference spectrum arise due to changes in the electronic spectrum of the quinoxaline derivative bound to the protein as compared to the electronic spectrum of the free quinoxaline. Thus, the difference spectrum can be used as the control to test for compounds that compete for the same binding site as quinoxaline derivative.

With the difference spectrum in hand as a control, a known amount of a test agent is added to a test well containing the receptor protein and the quinoxaline derivative. This reaction is allowed to equilibrate for a time and under conditions suitable for the test compound to bind to the receptor proteins (if it is capable of doing so). See the Examples for representative times, temperatures, etc. for the equilibration. A visible spectrum is than taken of the test well. This test spectrum is then compared to the control spectrum to see if they share the same characteristic changes in the electronic character of the quinoxaline. If the test spectrum shares the same features as the control spectrum, it indicates that the test compound displaced the quinoxaline derivative from the receptor protein. In this instance, the test compound would be considered a potential candidate for a receptor antagonist because the test compound has been shown capable of competitively binding to the receptor.

If the test spectrum does not share any features with the control spectrum, the test compound is incapable of displacing the quinoxaline derivative from the receptor. In this instance, the test compound cannot be considered a potential candidate for a receptor antagonist because the test compound is incapable of displacing the quinoxaline derivative from the receptor.

The sample to be tested can include the receptor protein in literally any form, so long as the receptor is available for binding to both the test compound and the quinoxaline derivative, including, without limitation: native, isolated, and enriched proteins, crude or purified, synthetic or semi-synthetic proteins, and truncated, fragmented, genetically recombinant, or otherwise genetically engineered proteins of any form. The receptor protein to be tested may comprise a fusion protein. The receptor protein may take the form of whole cell homogenates or lysates, or differential homogenates or lysates. The source of the receptor to be tested is not critical to the function of the invention, and source organisms can be prokaryotic, eukaryotic, unicellular, and multicellular. It is preferred that the present method be used to test the ability of compounds to bind to non-NMDA glutamate receptors.

EXAMPLES

The following Examples are included solely to provide a more complete and consistent understanding of the inventions disclosed and claimed herein. The Examples do not limit the scope of the invention in any fashion.

Materials and Methods:

Cortical neuronal cultures: Mixed cortical cell cultures containing both neurons and astrocytes were prepared from fetal mice (15–16 day gestation) as described by Asrari and Lobner (14). Briefly, dissociated cortical cells were plated on a preexisting astrocyte monolayer in a 24-well plate (a plating density of ~$2.5 \times 10^5$ cells per well). The plating medium was Eagle's minimal essential medium (MEM) (Earle's salts, supplied glutamine-free) supplemented with 5% fetal bovine serum, 5% horse serum, 2 mM glutamine and 20 mM glucose. Non-neuronal cell division was halted at 3–5 days in vitro by 3-day exposure to $10^{-5}$ M cytosine arabinoside. Cultures were maintained in humidified 5% $CO_2$ incubators at 37° C. and were used for experiments at 14–16 days in vitro.

GluR2-S1S2 Protein Preparation: GluR2-S1S2 is the protein that contains the ligand-binding domain of the GluR2 subunit of the glutamate receptor (15). The GluR2-S1S2 construct contains the S1 segment (amino acids 390 to 506 in the GluR2 sequence) and the S2 segment (amino acids 632 to 775 in the GluR2 sequence), with the two domains being linked together via a two-amino acid (GT) linker (16). The protein was expressed, purified, and characterized as described by Chen et al. (15).

Absorption measurements: The UV-visible absorption spectra were obtained using Agilent 8453 or Shimadzu UV 2501 spectrometers. The spectra were recorded in the 310 nm to 450 nm range, at a spectral resolution of 2 nm, using a 1 cm quartz cuvette as the sample holder.

EXAMPLE 1

Experiments with GluR2-S1S2

The absorption spectra were obtained using 0.4 to 1 mg/ml of GluR2-S1S2 in phosphate buffer at pH 7.4. The quinoxaline derivative used in this Example was CNQX, and the final concentration of CNQX in the protein/buffer was 20 to 30 µM.

To investigate the changes induced in the CNQX absorption spectrum due to the protein environment, a difference spectrum was generated between the absorption spectrum for CNQX in buffer and CNQX in the presence of GluR2-S1S2 (shown in FIG. 1, trace A). Because the difference features (in the spectrum shown in FIG. 1, trace A) arise due to changes in the electronic spectrum of CNQX bound to the protein relative to that of the free CNQX (in buffer), this difference spectrum can be used as the control to test for compounds that compete for the same binding site as CNQX.

A test compound competing for the same binding site as CNQX would displace the bound CNQX into the buffer and hence give rise to the same difference features as that shown in FIG. 1, trace A. In contrast, a test compound that does not bind competitively to the CNQX binding site will not displace the bound CNQX and hence no differences will be observed in the absorption spectrum due to the addition of such a test compound. In this Example, several known compounds that compete for the same site as CNQX were tested using the present invention, as were several compounds that do not bind to the GluR2-S1S2 (thus to illustrate the differences between compounds that bind to the receptor and compounds that do not).

Three difference spectra are shown in FIG. 1, traces B–D. These difference spectra were generated by taking the difference between the spectrum of receptor protein bound to 25 µM CNQX in the presence of a competitive ligand (50 µM) and the spectrum of the receptor protein in complex with 25 µM CNQX in the absence of the same ligand. The competitive ligands used were α-amino-3-hydroxy-5-methylisoxazole-4-propionic acid (AMPA) (trace B), glutamate (trace C), and kainate (trace D). The difference spectra for all three ligands are identical to the differences observed between the free and the bound spectra of CNQX (FIG. 1, trace A). These results clearly indicate that these three compounds (AMPA, glutamate, and kainite) displace CNQX from the protein and bind to the same site on the protein.

A similar difference spectrum between the spectrum of receptor protein bound to 25 µM CNQX in the presence of an inert, non-binding compound (50 µM of γ-amino butyric acid) and the spectrum of the protein in complex with 25 µM CNQX in the absence of the same compound was also obtained and is shown in FIG. 1, trace E. No difference features are observed, indicating that γ-amino butyric acid does not bind to the receptor protein and thus does not displace CNQX from the protein.

EXAMPLE 2

Experiments With Mouse Cortical Cells

Because the difference features between the free and protein-bound forms of CNQX occur in the visible region (generally from about 310 nm to about 450 nm), the same method used in Example 1 (where GluR2-S1S2 was used as the receptor protein) can be adapted for application to whole cell lysates or homogenates. In this Example, the same approach as in Example 1 was used, with the exception that rather than using GluR2-S1S2 as the receptor protein, the glutamate receptors present in mouse cortical cells were used. This Example thus shows that the subject invention can be used on whole-cell homogenates to determine if a test agent binds to non-MDMA receptors on the cells.

Dissociated mouse cortical cells were obtained as outlined in the Materials and Methods section. These cells in culture were washed and homogenized using a phosphate buffer (pH 7.4) solution containing 140 mM sodium chloride (PBS). The homogenized cells were diluted until the absorption in the 310 nm to 450 nm region was in the range of 0.5 to 0.8 absorption units. CNQX was added to the cells such that the final absorption of the sample in the 310 nm to 450 nm range was less than 1 absorbance unit. Difference absorption spectra were then obtained between the spectrum of cells with CNQX in the presence and the absence of the test compounds.

Figure 2:
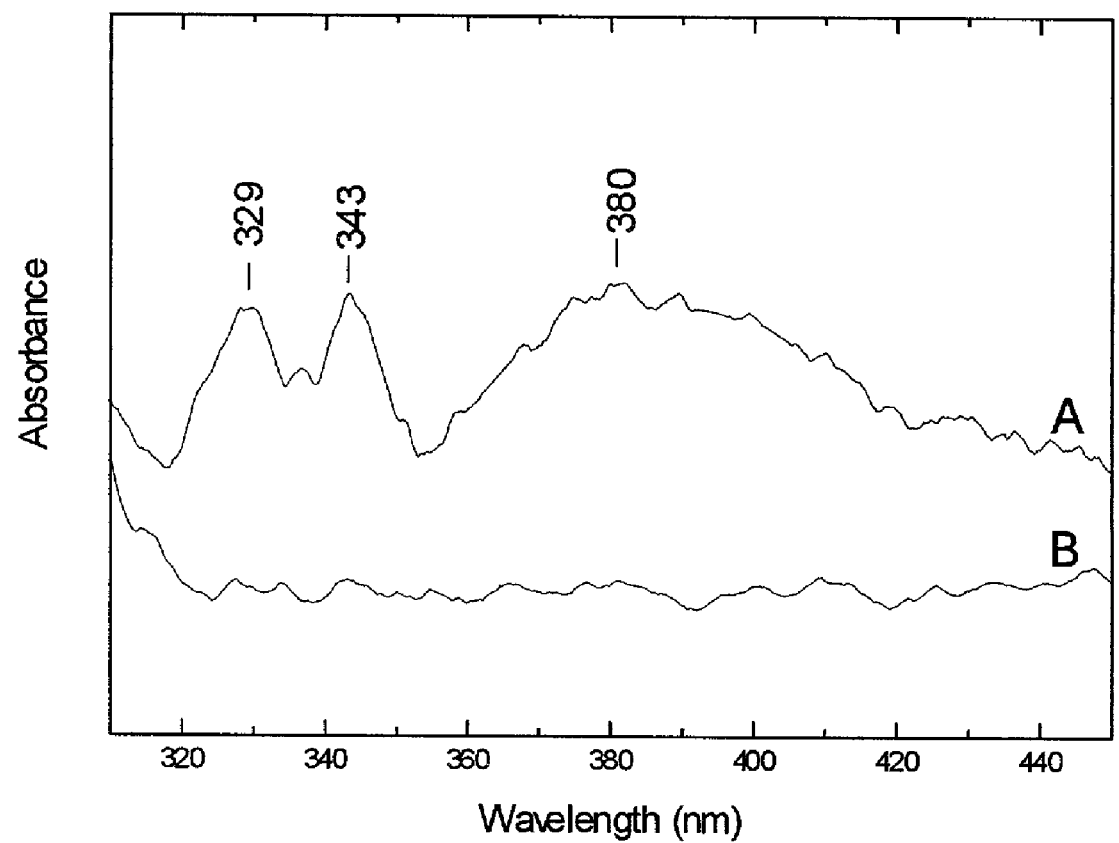
FIG. 2: (A) Difference spectrum between the mouse cortical cells in complex with 25 µM CNQX in the presence of glutamate and absence of glutamate. (B) Difference spectrum between the mouse cortical cells in complex with 25 µM CNQX in the presence of γ-amino butyric acid and absence of γ-amino butyric acid.

The compounds tested were glutamate (100 µM) (FIG. 2, trace A) and γ-amino butyric acid (100 µM) (FIG. 2, trace B). Glutamate is known to bind to the non-NMDA glutamate receptor of these cells. γ-Amino butyric acid is known not bind to the non-NMDA glutamate receptor, but does bind to γ-amino butyric acid receptors on these cells. The difference spectrum obtained for glutamate addition to the cortical cells containing CNQX (FIG. 2, trace A) is nearly identical to the differences observed between the free and the bound spectra of CNQX (see FIG. 1, trace A). This indicates that CNQX bound to the non-NMDA glutamate receptors in cortical cells is displaced by the addition of glutamate. In contrast, the difference spectrum between the spectra of the cortical cells in the presence CNQX before and after addition γ-amino butyric acid, exhibits no features in the 310 nm to 450 nm region. This result clearly indicates that CNQX is not displaced from the non-NMDA glutamate receptor by γ-amino butyric acid.

REFERENCES

1. Hollmann, M. & Heinemann, S. Cloned glutamate receptors. *Annu. Rev. Neurosci.* 17, 31–108 (1994).
2. Wisden, W. & Seeburg, P. H. Mammalian ionotropic glutamate receptors. *Curr. Opin. Neurobio.* 3, 291–298 (1993).
3. Hollmann, M., O'Shea-Greenfield, A., Rodgers, S. W. & Heinemann, S. Cloning by functional expression of a member of the glutamate receptor family. *Nature* 342, 643–648 (1989).
4. Keinänen, K. et al. A family of AMPA-selective glutamate receptors. *Science* 249, 556–560 (1990).
5. Boulter, J. et al. Molecular cloning and functional expression of glutamate receptor subunit genes. *Science* 249, 1033–1037 (1990).
6. Yoneda, Y. et al. Synthesis of diaminobutane derivatives as potent Ca(2+)-permeable AMPA receptor antagonists. *Bioorg Med Chem Lett* 11, 2663–2666. (2001).
7. Nakano, M., Ueda, H., Li, J. Y., Matsumoto, M. & Yanagihara, T. A potent AMPA/kainate receptor antagonist, YM90K, attenuates the loss of N-acetylaspartate in the hippocampal CA1 area after transient unilateral forebrain ischemia in gerbils. *Life Sci* 69, 1983–1990. (2001).
8. Rao, V. L., Dogan, A., Todd, K. G., Bowen, K. K. & Dempsey, R. J. Neuroprotection by memantine, a non-competitive NMDA receptor antagonist after traumatic brain injury in rats. *Brain Res* 911, 96–100. (2001).
9. Pringle, A. K., Self, J. & Iannotti, F. Reducing conditions produce a loss of neuroprotective efficacy of competitive but not non-competitive antagonists in a model of NMDA-mediated excitotoxicity in organotypic hippocampal slice cultures. *Acta Neurochir Suppl* 76, 79–80 (2000).
10. Ichord, R. N., Johnston, M. V. & Traystman, R. J. MK801 decreases glutamate release and oxidative metabolism during hypoglycemic coma in piglets. *Brain Res Dev Brain Res* 128, 139–148. (2001).
11. Uchida, K. et al. Dizocilpine but not ketamine reduces the volume of ischaemic damage after acute subdural haematoma in the rat. *Eur J. Anaesthesiol* 18, 295–302. (2001).
12. Winzor, D. J. & Sawyer, W. H. Quantitative characterization of ligand binding. (Wiley-Liss, New York; 1995).
13. Sakmann, B. & Neher, E. Single-channel recording. (New York: Plenum Press, 1995).
14. Asrari, M. & Lobner, D. Calcitonin potentiates oxygen-glucose deprivation-induced neuronal death. *Exp Neurol* 167, 183–188. (2001).
15. Chen, G. Q. & Gouaux, E. Overexpression of a glutamate receptor (GluR2) ligand binding domain in *Escherichia coli:* application of a novel protein folding screen. *Proc Natl Acad Sci USA* 94, 13431–13436 (1997).
16. Armstrong, N. & Gouaux, E. Mechanisms for activation and antagonism of an AMPA-sensitive glutamate receptor: crystal structures of the GluR2 ligand binding core. *Neuron* 28, 165–181. (2000).
17. Honore et al. Quinoxalinediones: potent competitive non-NMDA glutamate glutamate receptor antagonists. *Science* 241, 701 (1988).
18. Watkins et al. Structure-activity relationships in the development of excitatory amino acid receptor agonists and competitive antagonists. *TiPS* 11, 25 (1990).
19. Long et al. Effect of 6-cyano-2,3-dihydroxy-7-nitroquinoxaline (CNQX) on dorsal root-, NMDA-, kainate- and quisqualate-mediated depolarization of rat motoneurones in vitro. *Br. J. Pharmacol.* 100, 850 (1990).
20. King et al. Antagonism of synaptic potentials in ventral horn neurones by 6-cyano-7 nitroquinoxaline-2,3-dione: a study in the rat spinal cord in vitro. *Br. J. Pharmacol.* 107, 375 (1992).
21. Monaghan et al. The excitatory amino acid receptors: their classes, pharmacology and distinct properties in the function of the central nervous system. *Ann. Rev. Pharmacol. Toxicol.* 69, 365 (1989).
22. Nakanishi, Molecular diversity of glutamate receptors and implications for brain functions. *Science* 258, 597 (1992).
23. Pin and Duvoisin, The metabotropic glutamate receptors: structure and functions. *Neuropharmacology* 34, 1 (1995).
24. Knöpfel et al. Metabotropic glutamate receptors: novel targets for drug development. *J. Med. Chem.* 38, 1417 (1995).
25. Gill et al. The neuroprotective actions of 2,3-dihydroxy-6-nitro-7 sulfamoylbenzo-(f)-quinoxaline (NBQX) in a rat focal ischaemia model. *Brain Res.* 580, 35 (1992).
26. Zeman and Lodge, Pharmacological characterization of non-NMDA glutamate subtypes of glutamate receptors in the neonatal rat hemisected spinal cord in vitro. *Br. J. Pharmacol.* 106, 367 (1992).
27. Sheardown et al. The pharmacology of AMPA receptors and their antagonists. *Stroke* 24 Suppl I 146 (1993).
28. Namba et al. Antiepileptogenic and anticonvulsant effects of NBQX, a selective AMPA receptor antagonist, in the rat kindling model of epilepsy. *Brain Res.* 638, 36 (1994).

What is claimed is:

1. A method of measuring affinity of a test compound for a receptor protein, the method comprising:
    (a) providing a receptor-test compound complex comprising a non-NMDA glutamate receptor and a test compound bound thereto; then
    (b) contacting the receptor-test compound complex of step (a) with a known concentration of quinoxaline derivative selected from the group consisting of a compound of Formula I:

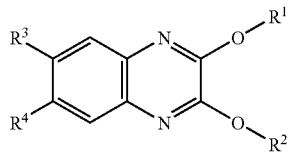

Formula I wherein R¹ and R² are independently selected from the group consisting of hydrogen; halo, substituted or unsubstituted alkyl, alkenyl, alkynyl; substituted or unsubstituted heteroalkyl; acyl; and substituted or unsubstituted aryl; and R³ and R⁴ are independently selected from the group consisting of hydrogen, hydroxy, halo; substituted or unsubstituted alkyl, alkenyl, alkynyl; substituted or unsubstituted heteroalkyl; acyl, carboxy, cyano, cyanoalkyl, nitro, amino, sulfonyl, alkylsulfonyl, amido, and sulfonamido;

under conditions wherein the quinoxaline derivative binds to the receptor, thereby yielding a receptor-quinoxaline complex and an amount of free quinoxaline derivative; and then (c) measuring the amount of the free quinoxaline derivative generated as a result of step (b), using visible absorption spectrophotometry, and comparing the amount of the free quinoxline to the known concentration of quinoxaline used in step (b), whereby the affinity of the test compound for the receptor is determined.

2. The method of claim 1, wherein a visible spectrum is taken at wavelengths ranging from about 315 to about 450 mu.

3. The method of claim 1, further comprising generating a control visible spectrum comprising a difference spectrum between a visible spectrum of the quinoxaline derivative ligand in the absence of the receptor and a visible spectrum of the quinoxaline derivative ligand bound to the receptor.

4. A method of measuring affinity of a test compound for a non-NMDA glutamate receptor protein, the method comprising:

(a) contacting a non-NMDA glutamate receptor with a known amount of a quinoxaline derivative under conditions wherein at least a portion of the quinoxaline derivative binds to the receptor, thereby yielding a receptor-quinoxaline complex and a first amount of free quinoxline derivative; then (b) recording a visible spectrum of the free quinoxline from step (a); then (c) contacting the complex of step (a) with a test compound under conditions and for a time sufficient to allow the test compound to bind to the receptor, thereby displacing at least a portion of the quinoxaline derivative from the complex and yielding a receptor-test compound complex and a second amount of free quinoxaline derivative;

(d) recording a visible spectrum of the free quinoxline derivative from step (c); and then (e) comparing the spectrum from step (b) wit the spectrum from step (d), whereby the affinity of the test compound for the receptor is determined.

5. The method of claim 4, wherein in step (a) the non-NMDA glutamate receptor is contacted with a quinoxaline derivative selected from the group consisting of a compound of Formula I:

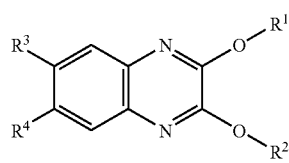

Formula I wherein R¹ and R² are independently selected from the group consisting of hydrogen; halo, substituted or unsubstituted alkyl, alkenyl, alkynyl; substituted or unsubstituted heteroalkyl; acyl; and substituted or unsubstituted aryl; and R³ and R⁴ are independently selected from the group consisting of hydrogen, hydroxy, halo; substituted or unsubstituted alkyl, alkenyl, ailcynyl; substituted or unsubstituted heteroalkyl; acyl, carboxy, cyano, cyanoalkyl, nitro, amino, sulfonyl, alkylsulfonyl, amido, and sulfonamido.

6. The method of claim 5, wherein R¹ and R² of the quinoxline derivative are hydrogen.

7. The method of claim 5, wherein the quinoxline derivative is selected from the group consisting of 6-cyano-7-nitro-2,3-dihydroxyquinoxaline; 6,7-dinitro-2,3-dihydroxyquinoxaline; and 6-nitro-2,3-dihydroxyquinoxaline-7-sulfonamide.

* * * * *